United States Patent [19]

Diamond et al.

[11] 4,342,964
[45] Aug. 3, 1982

[54] APPARATUS FOR ELECTROCHEMICAL MEASUREMENTS

[75] Inventors: Howard Diamond, Ann Arbor; Steven E. Enzer, Brooklyn; Joseph Flowers, Jr., Ann Arbor, all of Mich.

[73] Assignee: Transidyne General Corp., Ann Arbor, Mich.

[21] Appl. No.: 121,341

[22] Filed: Feb. 14, 1980

Related U.S. Application Data

[62] Division of Ser. No. 965,901, Dec. 14, 1978, Pat. No. 4,272,245.

[51] Int. Cl.³ .................................................. G01N 27/42
[52] U.S. Cl. ..................................... 324/450; 324/438
[58] Field of Search .................................. 324/438, 450

[56] References Cited

U.S. PATENT DOCUMENTS 3,781,659 12/1973 Ur ............................................ 324/450
3,941,665 3/1976 Eckfeldt ................................. 324/438
3,997,420 12/1976 Buzza .................................... 324/450

Primary Examiner—Michael J. Tokar
Attorney, Agent, or Firm—Krass, Young & Schivley

[57] ABSTRACT

A method and apparatus for measuring a chemical characteristic of a liquid such as its hydrogen ion activity or pH value. A disposable cassette having a reference and indicating electrode therein utilizes the same solution to first calibrate the device and then as an electrolytic bridge from the liquid sample to the reference electrode. The solution has the properties of a buffered pH and also provides a stable electrochemical environment around the reference electrode. In one embodiment, a volume of a liquid sample is placed into a capillary tube and the open end of the tube is then placed over the indicating electrode immersed in the solution. The electrical potential between the indicating electrode and the spaced reference electrode in the electrolyte solution provides a measurement of the pH value of the liquid when compared to the calibration potential previously measured without the liquid sample contacting the indicating electrode.

19 Claims, 7 Drawing Figures

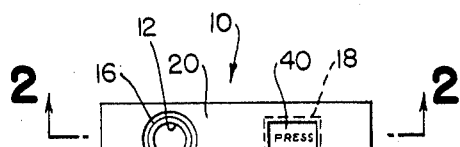
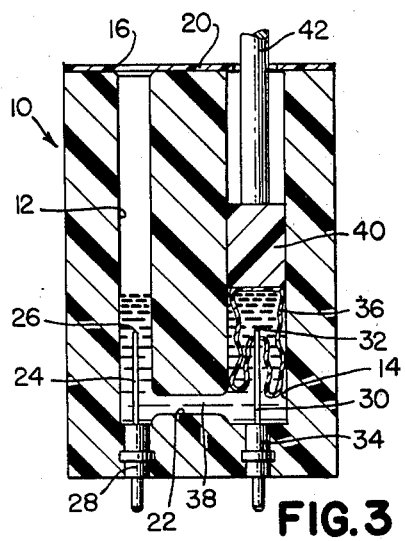
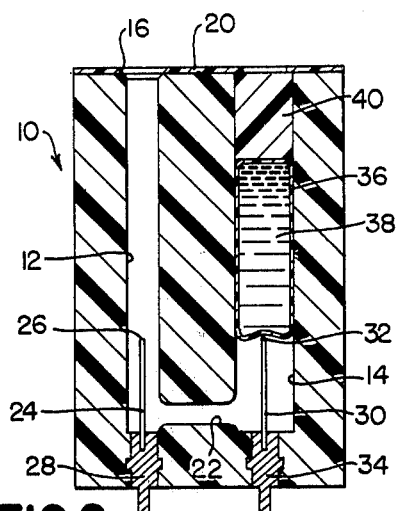
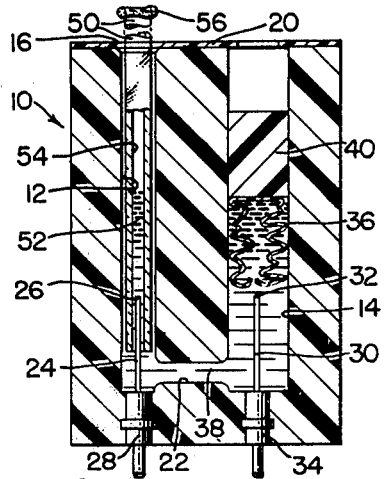
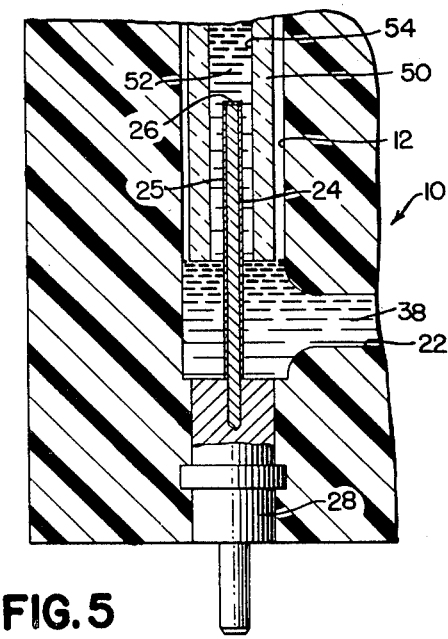
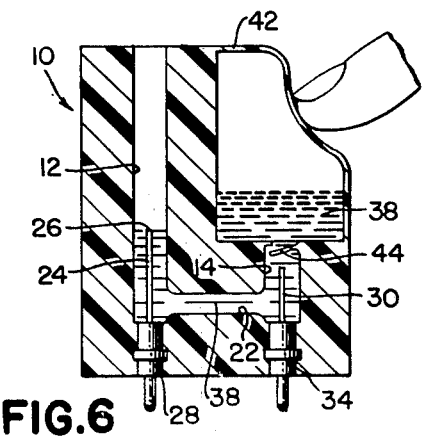

APPARATUS FOR ELECTROCHEMICAL MEASUREMENTS

This application is a division of application Ser. No. 965,901, filed Dec. 14, 1978, now U.S. Pat. No. 4,272,245 issued June 9, 1981.

BACKGROUND OF THE INVENTION

This invention relates to a method and apparatus for measuring a chemical characteristic of a liquid. More particularly, it relates to a method and apparatus for measuring the pH value of a blood sample.

The pH value of blood is a frequently measured physiological parameter which provides an indication of proper acid-base balance and blood-gas exchange through the lungs. In the field of obstetrics, such a test is often made if there are indications of fetal distress during labor which may be caused by the fetus not receiving sufficient oxygen from the mother through the placenta. In such cases, a blood sample is taken by making a small incision on the fetal scalp and placing a capillary tube in the proximity of the incision whereby the blood is drawn up into the interior portions of the tube through capillary action. The standard clinical device for measuring blood pH is the blood-gas analyzer such as the pH Blood Gas System and Supply manufactured by Corning Medical Corporation. Such analyzers require the transfer of the blood sample from the capillary tube to a receptacle in the instrument. As is known in the art, if any ambient air mixes with the blood sample, the pH value will change. Hence, there is a good possibility of contaminating the blood sample during the transfer from the original collecting device to the instrument. Moreover, since such analyzers are complex and costly devices, they are typically located only in the hospital lab where they need to be operated by a skilled technician. As a result, there is often considerable delay between the time of taking the blood sample until the results from the lab are received. Of course, such delays are undesirable in emergency situations.

U.S. Pat. Nos. 3,911,901 to Niedrach et al, 3,049,118 to Arthur et al, and 3,399,667 to Nishimoto et al disclose representative devices for measuring the pH value of blood samples. However, they have all been relatively complex and costly to manufacture. Moreover, their use has been limited to trained personnel. Furthermore, none of them have permitted direct pH measurement from the same device which collected the blood sample. Another drawback in many of the prior art devices is that they required large quantities of the liquid to be tested. Unfortunately, it is often difficult to readily obtain sizable samples.

OBJECTS AND SUMMARY OF THE INVENTION

Therefore, it is the primary object of this invention to provide a method and apparatus for measuring the chemical characteristics of a liquid, such as the pH value of a blood sample, in which the measurement is taken from the liquid in the same device in which it was collected.

It is another object of this invention to permit such measurements to be taken from a relatively small sample quantity.

It is a further object of this invention to provide a method and apparatus for inexpensively accomplishing the above objective without necessitating the use of trained personnel.

According to the broadest aspect of this invention, the chemical characteristic measurement is taken by first calibrating the test apparatus by measuring the electrical potential established when an indicating and reference electrode are immersed in a solution. It is a feature of this invention that the solution provides a two-fold purpose: first, to calibrate the electrodes and secondly, to provide an electrolytic bridge between the liquid sample and the reference electrode. After calibration, the liquid sample is brought into contact with the indicating electrode. According to another aspect of this invention, the device is designed so that the sample is introduced in such a manner so as to remove the solution which would otherwise be contacting the indicating electrode. The solution does, however, remain in the device and provides an electrolytic bridge from the liquid sample to the reference electrode. Accordingly, the potential thus established, when compared to the previously taken calibration factor, provides an accurate indication of the chemical characteristic of the liquid sample. This technique can be utilized by relatively inexperienced personnel, does not require large quantities of the liquid sample, and may be embodied in inexpensive apparatus which may be disposable.

In one embodiment of this invention, the sample is collected in a capillary tube. The open end of the capillary tube containing the sample is placed over one end of the indicating electrode immersed in the electrolyte solution along with the spaced reference electrode. A disposable cassette is provided for housing the two electrodes. The indicating electrode is disposed in a guide channel for positioning the end of the capillary tube over the indicating electrode. Preferably, means are provided for introducing the electrolyte solution into the cassette to cover both electrodes whereby a first calibrating potential is established therebetween. When the capillary tube is placed over the indicating electrode, the liquid sample displaces the solution so that a subsequently taken measurement is derived from the half-cell potential between the sample and indicating electrode due to the chemical characteristic of the sample. The solution is buffered near the expected pH value of the liquid and further provides a stable electrochemical environment for the reference electrode.

BRIEF DESCRIPTION OF THE DRAWINGS

These and other objects and advantages of the present invention will become more apparent upon reading the following specification and by reference to the drawings in which:

FIG. 1 is a top plan view of one embodiment of the apparatus for this invention;

FIG. 2 is a cross-sectional view along the lines 2—2 of FIG. 1;

FIG. 3 is a view of the apparatus shown in FIG. 2 illustrating one manner of introducing the electrolyte into the apparatus;

FIG. 4 is a view similar to FIG. 3 which illustrates the capillary tube being placed over the indicating electrode;

FIG. 5 is an enlarged partial cross-sectional view of FIG. 4 illustrating the capillary tube-indicating electrode engagement;

FIG. 6 is a cross-sectional view illustrating another embodiment of the apparatus of this invention.

DESCRIPTION OF THE PREFERRED EMBODIMENTS

Figure 7:
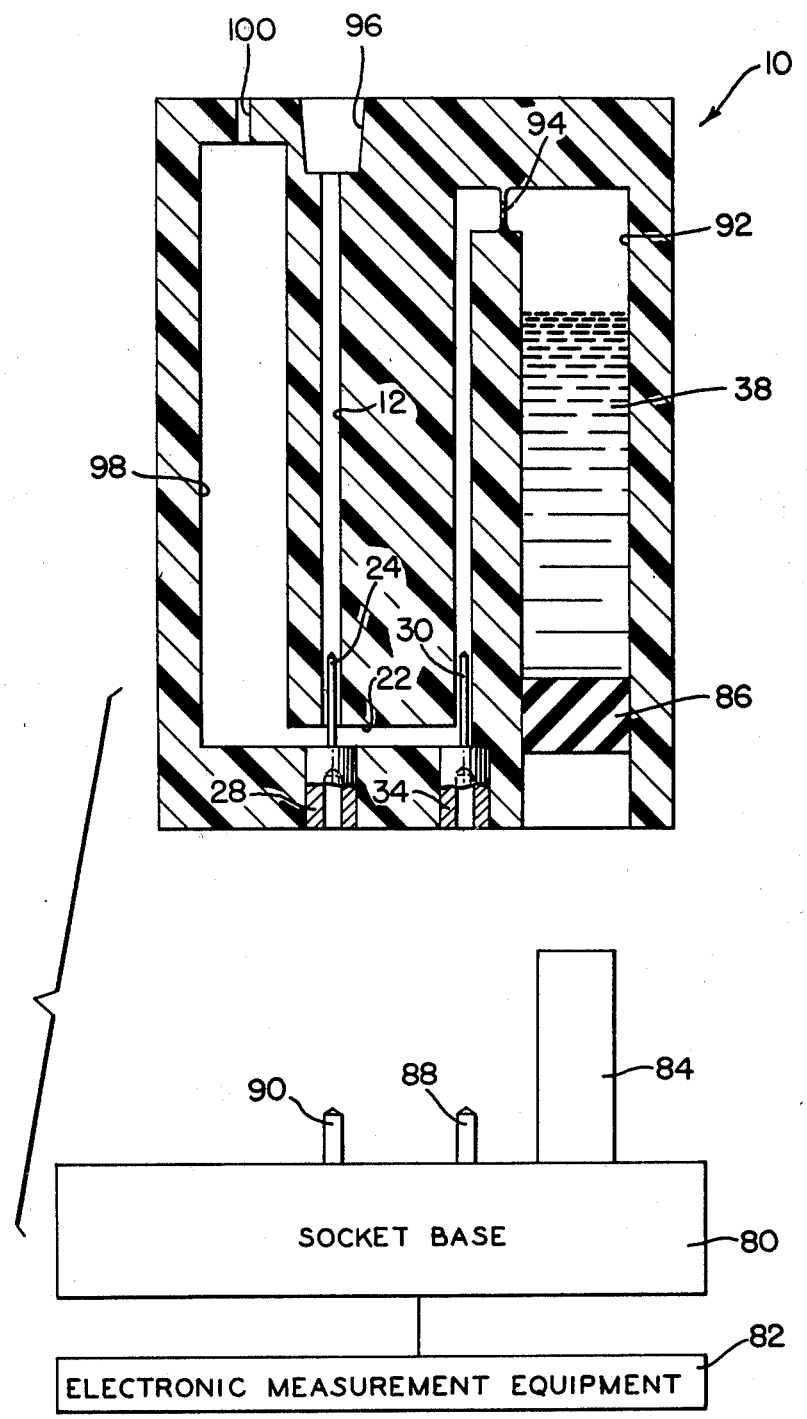
FIG. 7 is an exploded cross-sectional view of still another embodiment of this invention.

Referring now to FIGS. 1 and 2, there is shown a box-like cassette 10 which is preferably made of plastic. Cassette 10, in this embodiment, includes two longitudinally extended channels 12 and 14, which terminate at one end in openings 16 and 18, respectively, at top cover 20. Bottom portions of channels 12 and 14 are connected by a transverse bridging chamber 22.

An indicating electrode 24 is centrally disposed along the major longitudinal axis of channel 12 and projects from the bottom portion of chamber 22 upwardly into the confines of channel 12. Indicating electrode 24, according to one aspect of this invention, is a stainless steel rod which is made by first coating the outer surface thereof with an insulating resin 25 such as EPOXYLITE's No. 6001-M Electrode Insulator solution which may be applied and cured according to manufacturer's specifications. The tip of the rod is then polished by known methods such as with a grinding wheel to remove resin therefrom. The upper portion of the rod is then placed into an electrolytic solution containing antimony and a potential is established between the rod and the electrolyte. Since only the exposed tip is conductive, a layer (see FIG. 5) of antimony is electroplated only onto the tip 26 of the rod serving as indicator electrode 24.

In this embodiment, lower portions of the rod are press fit into a conductive connector 28 to provide electrical connection to external circuitry. In order to provide better electrical contact between electrode 24 and connector 28, the insulating resin 25 is removed from lower portions of electrode 24 at the mating interface with connector 28. Alternatively, the electrodes may be mounted in their respective connectors prior to the above described electroplating procedure Accordingly, the tip 26 of indicating electrode 24 is disposed within confines of guide channel 12 and provides the only chemically reactive portion of electrode 24. As will become more apparent later herein, the diameter of guide channel 12 is slightly larger than the outside diameter of the well-known capillary tubes used to take blood samples. The diameter of electrode 24 is slightly smaller than the inside diameter of the capillary tube. For a capillary tube having an outside diameter of 1.5 mm and an inside diameter of 1.1 mm, the diameter of guide tube 12 may be about 1.6 mm whereas the diameter of electrode 24 may be about 0.25 mm. It should be noted that these dimensions are given merely for illustrative purposes and that no limitation is intended thereby.

A reference electrode 30 similarly has a tip portion 32 disposed in channel 14 and lower portions thereof coupled to a connector 34. Reference electrode 30 can be made of a variety of metal-metal salt materials which develop a stable half-cell potential when immersed in an electrolyte. Preferably, reference electrode 30 is a silver wire having a silver-chloride coating. Such electrodes are well known in the art. In the embodiment shown in FIGS. 1-5, reference electrode 30 is a rigid structure having a pointed tip 32.

A capsule 36 having a breakable membrane is disposed in channel 14 above tip 32 of reference electrode 30. In accordance with this preferred embodiment, capsule 36 contains a sufficient amount of electrolyte 38 to cover electrodes 24 and 30 when the membrane is broken as shown in FIG. 3. As shown in FIG. 3, capsule 36 may be broken by pushing a rod 42 against a slidable stopper 40 which, in turn, urges capsule 36 against electrode tip 32 to break the capsule membrane and introduce the electrolyte 38 into interior portions of the cassette 10. Other means for immersing electrodes 24 and 30 in the electrolyte 38 can be readily envisioned. For example, FIG. 6 shows an alternative embodiment for cassette 10 in which common reference numerals are utilized to identify common elements. In this alternative embodiment, a flexible pouch 42 contains electrolyte 38. A one-way valve flap 44 interfaces channel 14 with pouch 42 in such a way that upon squeezing pouch 42, the electrolyte 38 flows into channel 12, 14 and chamber 22 to cover electrodes 24 and 30. It should be noted that in this embodiment, reference electrode 30 need not be rigid since it is not needed to puncture capsule 36 shown in the previous embodiment.

FIG. 7 illustrates still another embodiment where socket 80 coupled to suitable electronic measurement equipment 82 includes a rod 84 which presses upwardly on piston 86 when cassette 10 is inserted thereon with pins 88 and 90 engaging connectors 34 and 28, respectively. The solution 38 is contained in a chamber 92 above piston 86 such that upon placement of cassette 10 on socket 80, piston 86 causes the solution 38 to break membrane 94 and cover electrodes 24 and 30. In this embodiment, guide channel 12 includes a relief 96 which conforms to the connector portion of a syringe (not shown) which may be used as an alternate source of supplying the liquid sample. The embodiment of FIG. 7 also includes an overflow chamber 98 coupled to chamber 22 and includes an air vent 100 to equalize the pressures within cassette 10.

According to still another aspect of this invention, the electrolyte 38 is buffered at a pH value near the middle of the physiological range. Furthermore, electrolyte 38 includes substantially the same reactant ion concentration that is about the same as that of the liquid to be tested. In this embodiment, where the reference electrode 30 is a silver/silver-chloride mixture, the reactant ions are chloride ions. The reactant ions are those ions which develop the half-cell potential with the reference electrode. As will be more fully understood herein, diffusion of the reactant ions in the sample under test is prevented from reaching the reference electrode which may, in turn, disturb the accuracy of the measurement. Where the liquid under test is blood, electrolyte 38 is preferably an aqueous solution of tris (hydroxymethyl) aminomethane $(CH_2OH)_3CNH_2$, hydrochloric acid and sodium chloride. The tris is available from a variety of chemical manufacturers and is known in the art. The electrolyte 38 may be prepared by providing a 0.1 Normal tris solution by dissolving 121.14 mg of the tris in 1,000 ml of distilled water. A 0.01 Normal solution of hydrochloric acid is prepared by diluting 10 ml of 1.0 Normal hydrochloric acid with 1,000 ml of distilled water. In repairing the electrolyte, the tris and hydrochloric acid solution may be mixed together in varying quantities according to the following table to provide a buffer solution pH value between 7 and 9.

TABLE I

| pH/25° C. | Tris, 0.1 N | HCl .01 N |
| --- | --- | --- |
| 7.00 | 50.0 ml | 46.6 ml |
| 7.10 | 50.0 | 45.7 |

TABLE I-continued

| pH/25° C. | Tris, 0.1 N | HCl .01 N |
|---|---|---|
| 7.20 | 50.0 | 44.7 |
| 7.30 | 50.0 | 43.7 |
| 7.40 | 50.0 | 42.0 |
| 7.50 | 50.0 | 40.3 |
| 7.60 | 50.0 | 38.5 |
| 7.70 | 50.0 | 36.6 |
| 7.80 | 50.0 | 34.5 |
| 7.90 | 50.0 | 32.0 |
| 8.00 | 50.0 | 29.2 |
| 8.10 | 50.0 | 26.2 |
| 8.20 | 50.0 | 22.9 |
| 8.30 | 50.0 | 19.9 |
| 8.40 | 50.0 | 17.2 |
| 8.50 | 50.0 | 14.7 |
| 8.60 | 50.0 | 12.1 |
| 8.70 | 50.0 | 10.3 |
| 8.80 | 50.0 | 8.5 |
| 8.90 | 50.0 | 7.0 |
| 9.0 | 50.0 | 5.7 |

Consequently a buffer solution having an approximate 10/1 to 1/1 ratio of tris to hydrochloric acid has been found to provide pH value of between 7 and 9. Preferably, the buffer solution should have a pH value between 7.2 and 7.5, more specifically about 7.3, which correlates to the normally encountered pH values of blood.

Sodium chloride is then added to the buffer solution in order to supply a chloride ion concentration substantially the same as that found in human blood, that being approximately 103 milliequivalents meq. It has been found that about 252 mg of sodium chloride per 100 ml of the buffer solution should provide the desired 103 meq chloride ion concentration for a 7.30 pH solution. It is understood, however, that these numbers are only by way of a specified example and should not be construed as limiting. For example, the quantity of sodium chloride depends upon the quantity of HCl used to determine the pH of the solution.

It should be noted that variations of the above example will become apparent to one skilled in the art depending for example, upon the electrode materials utilized and the liquid to be tested. According to the teachings of this invention, to the extent the liquid to be measured contains an ion that may react with the reference electrode, and thus produce an erroneous reading of the property to be measured, electrolyte 38 should have a concentration of that reactive ion substantially the same as that contained by the liquid to prevent migration of the liquid's reactive ions to the reference electrode such that the reference measurement is unaffected by the reactive ion. Specifically, with relationship to the preferred embodiment, the chloride ion concentration should be substantially the same as that of blood. The pH value of the electrolyte should closely approximate that of the liquid under test. Preferably, the pH value of the electrolyte 38 should be approximately between 7 and 9, and more specifically, between 7.2 and 7.5, when the liquid under test is blood. However, it is important that the pH value of electrolyte 38, whatever it is, be stable since it is used as a constant in the test liquid measurement as will now be described.

According to the method of this invention, electrolyte 38 is introduced into cassette 10 to cover both indicating electrode 24 and reference electrode 30. This can be accomplished, for example, as shown in FIG. 3 by pressing capsule against electrode 30 to burst the capsule 36 containing electrolyte 38. Alternatively, as shown in FIG. 6 pouch 42 can be squeezed to force electrolyte 38 into interior portions of the cassette 10 containing electrodes 24 and 30. As shown in the embodiment of FIG. 7, the electrolyte 38 is introduced when cassette 10 is placed on socket 80. It should be noted that while it is a feature of this invention that electrolyte 38 is self-contained with cassette 10, the electrolyte can be introduced by other external means.

A calibration potential is thus established between electrodes 24 and 30. As is known in the art, the potential difference between these electrodes is due to the two half-cell EMF's established between the indicating electrode 24 and electrolyte 38, and the reference electrode 30 and the electrolyte 38. This potential can be measured by straight forward electronic techniques by coupling connectors 28 and 34 to the external measuring circuitry 82. Preferably, the circuitry first measures the output potential and makes two calibrating checks. First, it makes sure that the potential is within predetermined high-low limits. Secondly, it checks the rate of drift of the potential measurement and insures that it is below a certain drift factor. Then, it solves the following equation for C:

$$V = K[\text{pH}] + C$$

Where:
V is the measured potential;
pH is the known pH value of electrolyte 38;
K is a constant associated with the electrode sensitivity; and
C is a calibration constant.

The calculated value of C is then stored, for example, in a known random access memory (RAM), for later retrieval purposes. It should be noted that this invention only requires a single-point calibration of the electrodes since electrolyte 38 is buffered at the middle of the most critical region in which the device operates and the expected range of chemical values from the test liquid is relatively narrow. However, a two-point calibration can be made, if desired, depending on the test liquid to account for different electrode sensitivites. However, where the apparatus of the present invention is utilized to measure the pH of blood, only the single-point technique is required which measures the offset potential difference between the electrodes utilized.

In the embodiments of FIGS. 1–6, capillary tube 50 which has previously collected blood sample 52 in its bore 54, is then placed in guide channel 12 via opening 16. Capillary tube 50 may include a wax-like stopper 56 on its upper portion to close one end of tube 50 in order to maintain blood 52 in bore 54 as is known in the art. Tube 50 is then slid along guide tube 12 until tip 26 of indicating electrode 24 protrudes into tube bore 54 to engage the blood 52 therein as can be seen in FIGS. 4 and 5. As can be seen most clearly in FIG. 5, the relative dimensions of guide tube 12 and electrode 24 with respect to tube 50 automatically centers tube 50 in channel 12 to provide unobstructed engagement with tip 26 of electrode 24. When tube 50 slides over electrode 24, the electrolyte 38 is displaced so that only blood 52 contacts the chemically active tip 26 of electrode 24. Consequently, a new half-cell potential is established between electrode 24 and blood 52. However, the same half-cell potential remains at the interface between reference electrode 30 and electrolyte 38. In the embodiment of FIG. 7, the connector of the syringe is seated on relief 96 and the blood in the syringe is forced into channel 12, thereby displacing the electrolyte 38 from indicating electrode tip 26.

It can now be understood that by providing the same chloride concentration in electrolyte 38 as that of blood 52, the migration of the chloride ions in blood 52 to reference electrode 30 is prevented which might disturb the original half-cell potential which was used to provide the calibration potential. Accordingly, the same electrolyte 38 can be used as both a calibrating solution and as a bridge between blood 52 and reference electrode 30 during the pH measurement. This measurement is accomplished by again sensing the electrical potential between electrodes 24 and 30. Since the calibration constant C was calculated in the prior calibration measurement, the pH value of the blood 52 can be calculated by solving for pH in the equation set forth above. The electronics in measuring apparatus 82 can be conventionally set up to retrieve the value of C previously stored in the memory and insert it into the equation, with the apparatus solving for the value of pH using well known techniques. The cassette 10 may remain on socket 82 during both the calibration step and pH measurement step. The operator may merely push a button (not shown) which causes the calculation of C, subsequently introduce the blood into cassette 10, and thereafter press another button (not shown) to take the pH measurement of the sample. The sensed pH value can then be displayed by suitable devices in the measuring equipment 82.

It is now readily apparent that the present invention provideds a relatively inexpensive means by which chemical characteristics of a liquid can be measured. The cassette 10, including electrodes 24 and 30, can be inexpensively manufactured so that it may be disposable. Moreover, the tests can be accomplished by relatively inexperienced personnel. Even more importantly, since the measurement is taken from the same device in which the sample is collected, the possibility of contamination is greatly decreased. Equally important is that the present invention provides a device which is capable of providing these measurements from extremely small sample sizes. It should be understood that obvious modifications to the unique concepts described herein may become apparent to one skilled in the art. Therefore, while this invention has been described in connection with particular examples thereof, no limitation is intended thereby except that as defined in the following claims.

What is claimed is:

1. A device for measuring chemical characteristics of a liquid, said device comprising:
   a housing having upper and lower end surfaces;
   a longitudinally extending channel in said housing terminating at one end thereof at least upper surface of the housing and adapted to receive a capillary tube containing a sample of the liquid;
   an indicating electrode located about the longitudinal axis of said channel, with said indicating electrode having a tip projecting upwardly into said channel;
   a reference electrode spaced from said indicating electrode;
   a chamber in said housing bridging said reference and indicating electrodes;
   means for introducing an electrolyte into said chamber to cover said electrodes; and
   wherein said channel is adapted to guide an open end of the capillary tube containing the liquid into engagement with the tip of the indicating electrode to displace the electrolyte therefrom whereupon an electrical property is established between the electrodes encompassing the electrolyte which is indicative of the chemical characteristic of the liquid.

2. The device of claim 1 wherein the liquid is blood and the chemical characteristic is its pH value.

3. The device of claim 2 wherein said indicating electrode comprises a rigid rod coated about its circumference with an insulating material and wherein the tip of said rod has a layer of a chemically active material thereon.

4. The device of claim 3 wherein said chemically active material is antimony.

5. The device of claim 1 wherein said reference electrode is comprised of silver/silver-chloride.

6. The device of claim 2 wherein said electrolyte has a concentration of ions reactant with the reference electrode substantially the same as blood to thereby prevent diffusion of said reactant ions in the blood to said reference electrode.

7. The device of claim 5 wherein said electrolyte has a chloride ion concentration substantially the same as that of blood.

8. The device of claim 7 wherein said electrolyte has a pH value in the range between 7 and 9.

9. The device of claim 1 wherein said electrolyte is contained in a sealed member carried by the housing and adapted to be ruptured to cover the electrodes with said electrolyte.

10. The device of claim 1 which further comprises connector means coupled to said electrodes for providing electrical connection to external circuitry.

11. Apparatus for measuring chemical characteristics of a liquid, said apparatus comprising:
    a cassette containing spaced indicating and reference electrodes;
    means containing an electrolyte solution; and
    socket means for receiving said cassette, said socket means including means for making electrical connection to said electrodes and for causing said electrolyte solution to cover the electrodes when the cassette is inserted in the socket.

12. The apparatus of claim 11 which further comprises:
    electronic measurement means connected to the socket for measuring an electrical property between the electrodes.

13. The apparatus of claim 12 wherein said cassette includes a channel for guiding a capillary tube containing the liquid onto a tip of said indicating electrode.

14. The apparatus of claim 13 wherein said electronic measurement means is adapted to measure the electrical property first established between the electrodes when covered by the electrolyte solution to establish a calibration factor and to secondly measure the subsequently established electrical property between the electrodes when the liquid is contacting said indicating electrode whereby the chemical characteristics of the liquid may be derived from said measurements.

15. A device for measuring chemical characteristics of a liquid comprising a housing containing spaced indicating and reference electrodes bridged by a chamber; and a sealed member containing an electrolyte solution, said member being adapted to be broken to introduce the electrolyte into the chamber to cover the electrodes.

16. The device of claim 15 wherein said member is carried by said housing.

17. The device of claim 15 which further includes a channel for guiding a capillary tube containing the liquid onto a tip of the indicating electrode.

18. A machine for measuring electrochemical characteristics of a liquid, said machine being adapted to receive a cartridge containing spaced indicating and reference electrodes, said cartridge carrying a container filled with an electrolyte solution initially isolated from said electrodes, said machine comprising:

means for making electrical connection with said electrodes;

means for urging said electrolye from said container to cover both of said electrodes with the electrolyte;

means for measuring a first electrial property developed between the electrodes bridged by the electrolyte thereby establishing a calibration factor; and means for measuring a second electrical property developed between the electrodes when the indicating electrode comes into contact with the liquid to be measured whereby the chemical characteristics of the liquid can be calculated from the first and second electrical properties.

19. The machine of claim 18 which includes a receptacle for making electrical connection with said electrodes and for breaking the integrity of said container to cover the electrodes with the electrolyte when the cartridge is inserted into the receptacle.

* * * * *